US012396632B2

(12) United States Patent
Schelter et al.

(10) Patent No.: US 12,396,632 B2
(45) Date of Patent: Aug. 26, 2025

(54) ENHANCED VISUALIZATION METHODS AND SYSTEMS FOR ENDOSCOPIC PROCEDURES

(71) Applicants: John Schelter, Centennial, CO (US); Matthew Provencher, Edwards, CO (US)

(72) Inventors: John Schelter, Centennial, CO (US); Matthew Provencher, Edwards, CO (US)

( * ) Notice: Subject to any disclaimer, the term of this patent is extended or adjusted under 35 U.S.C. 154(b) by 0 days.

(21) Appl. No.: 17/029,984

(22) Filed: Sep. 23, 2020

(65) Prior Publication Data
US 2021/0085164 A1  Mar. 25, 2021

Related U.S. Application Data

(60) Provisional application No. 62/904,421, filed on Sep. 23, 2019.

(51) Int. Cl.
A61B 1/313 (2006.01)
A61B 1/00 (2006.01)
A61B 1/045 (2006.01)

(52) U.S. Cl.
CPC ........ *A61B 1/3132* (2013.01); *A61B 1/00009* (2013.01); *A61B 1/00016* (2013.01); *A61B 1/0005* (2013.01); *A61B 1/00149* (2013.01); *A61B 1/045* (2013.01); *A61B 1/00163* (2013.01)

(58) Field of Classification Search
CPC ............ A61B 1/00009; A61B 1/00016; A61B 1/00018; A61B 1/00045; A61B 1/0005; A61B 1/00114; A61B 1/00149; A61B 1/00163; A61B 1/045; A61B 1/05; A61B 1/0684; A61B 90/37; A61B 90/50; A61B 2090/364; A61B 2090/371; A61B 17/3432; A61B 2017/3429; A61B 1/3132; A61B 1/317

See application file for complete search history.

(56) References Cited

U.S. PATENT DOCUMENTS

| 4,863,133 | A | | 9/1989 | Bonnell |
| 5,184,601 | A | | 2/1993 | Putnam |
| 5,441,042 | A | | 8/1995 | Putnam |
| 5,447,149 | A | | 9/1995 | Kikawada et al. |
| 5,785,643 | A | | 7/1998 | Lynn |
| 5,797,835 | A | * | 8/1998 | Green ................ A61B 1/00119 600/113 |
| 8,156,439 | B2 | | 4/2012 | Booth |
| 9,492,065 | B2 | | 11/2016 | Tesar et al. |
| 9,986,892 | B2 | | 6/2018 | Gilreath et al. |
| 10,092,167 | B2 | | 10/2018 | Kirma et al. |

(Continued)

FOREIGN PATENT DOCUMENTS

EP  3689219 A1  8/2020

OTHER PUBLICATIONS

U.S. Appl. No. 62/904,421, filed Sep. 23, 2019. First Named Inventor: Schelter.

*Primary Examiner* — Aaron B Fairchild
(74) *Attorney, Agent, or Firm* — Santangelo Law Offices, P.C.

(57) ABSTRACT

Embodiments of the present invention provide enhanced visualization of laparoscopic space or the like perhaps with multiple camera views on a screen or multiple screens, a camera box, scopes, or the like.

6 Claims, 5 Drawing Sheets

(56) References Cited

U.S. PATENT DOCUMENTS

| | | |
|---|---|---|
| 10,412,290 B2 | 9/2019 | Sidar |
| 10,499,794 B2 | 12/2019 | Gilreath et al. |
| 2005/0171470 A1* | 8/2005 | Kucklick ............ A61B 1/00135 604/263 |
| 2006/0058617 A1* | 3/2006 | Sano .................... A61B 1/0005 600/407 |
| 2008/0270912 A1 | 10/2008 | Booth |
| 2009/0088634 A1* | 4/2009 | Zhao ................. A61B 1/00193 600/425 |
| 2012/0059361 A1* | 3/2012 | Yacoubian ........... A61B 5/1075 606/1 |
| 2013/0109916 A1 | 5/2013 | Levy |
| 2013/0116506 A1* | 5/2013 | Bayer ................. A61B 1/0623 600/113 |
| 2014/0213850 A1 | 7/2014 | Levy et al. |
| 2014/0303491 A1* | 10/2014 | Shekhar ................. G06T 7/337 600/424 |
| 2014/0357984 A1* | 12/2014 | Wallace ................ G16H 20/40 600/424 |
| 2015/0049167 A1* | 2/2015 | Suzuki ................ A61B 1/0057 348/45 |
| 2015/0164308 A1 | 6/2015 | Ratnakar |
| 2016/0278611 A1* | 9/2016 | Power ................ G06F 3/04886 |
| 2018/0256008 A1* | 9/2018 | Nishizawa ................ G06T 7/73 |
| 2018/0368656 A1* | 12/2018 | Austin ................ A61B 90/361 |
| 2019/0008367 A1* | 1/2019 | Ishikawa .......... A61B 1/000094 |
| 2019/0388162 A1* | 12/2019 | Azizian ................. A61B 34/37 |
| 2020/0000325 A1 | 1/2020 | Levy et al. |
| 2020/0022570 A1* | 1/2020 | Kennedy ............ A61B 1/00193 |
| 2020/0221940 A1* | 7/2020 | Kennedy ............ G02B 23/2484 |
| 2020/0222146 A1* | 7/2020 | Komp ............. A61B 1/000094 |
| 2020/0390503 A1* | 12/2020 | Casas ..................... A61B 17/72 |

* cited by examiner

ENHANCED VISUALIZATION METHODS AND SYSTEMS FOR ENDOSCOPIC PROCEDURES

PRIORITY CLAIM

This is a U.S. Nonprovisional patent application claiming priority to and the benefit of U.S. Provisional Patent Application No. 62/904,421 filed Sep. 23, 2019, hereby incorporated by reference herein.

BACKGROUND OF THE INVENTION

Traditional arthroscopic/laparoscopic procedures may utilize multiple portals with a single visualization portal ("scope portal") and camera box with a single input and output. However, for a surgeon to accurately assess and even repair the pathology of the joint (or laparoscopic space or the like), the surgeon may frequently need move the scope portal multiple times within a given procedure in order to accurately assess and complete the repair. Current cameras utilized can vary between about 0 degrees and about 70 degrees. When anything other than a 0-degree scope may be used, the view may be slightly skewed from what could actually be seen by the human eye.

Since switching between portals requires time and potential complications, many surgeons elect to view the entire procedure through a single portal. However, based on later cadaver dissections of these repairs in the laboratory over the past 15 years, many surgeons have been disappointed as to the final result of their surgeries.

BRIEF SUMMARY OF THE INVENTION

The present invention includes a variety of aspects, which may be selected in different combinations based upon the particular application or needs to be addressed.

An object of the present invention may be to provide more than one camera view of a joint or other laparoscopic area.

Naturally, further objects, goals and embodiments of the inventions are disclosed throughout other areas of the specification, claims, and drawings.

DETAILED DESCRIPTION OF THE INVENTIONS

Figure 1:
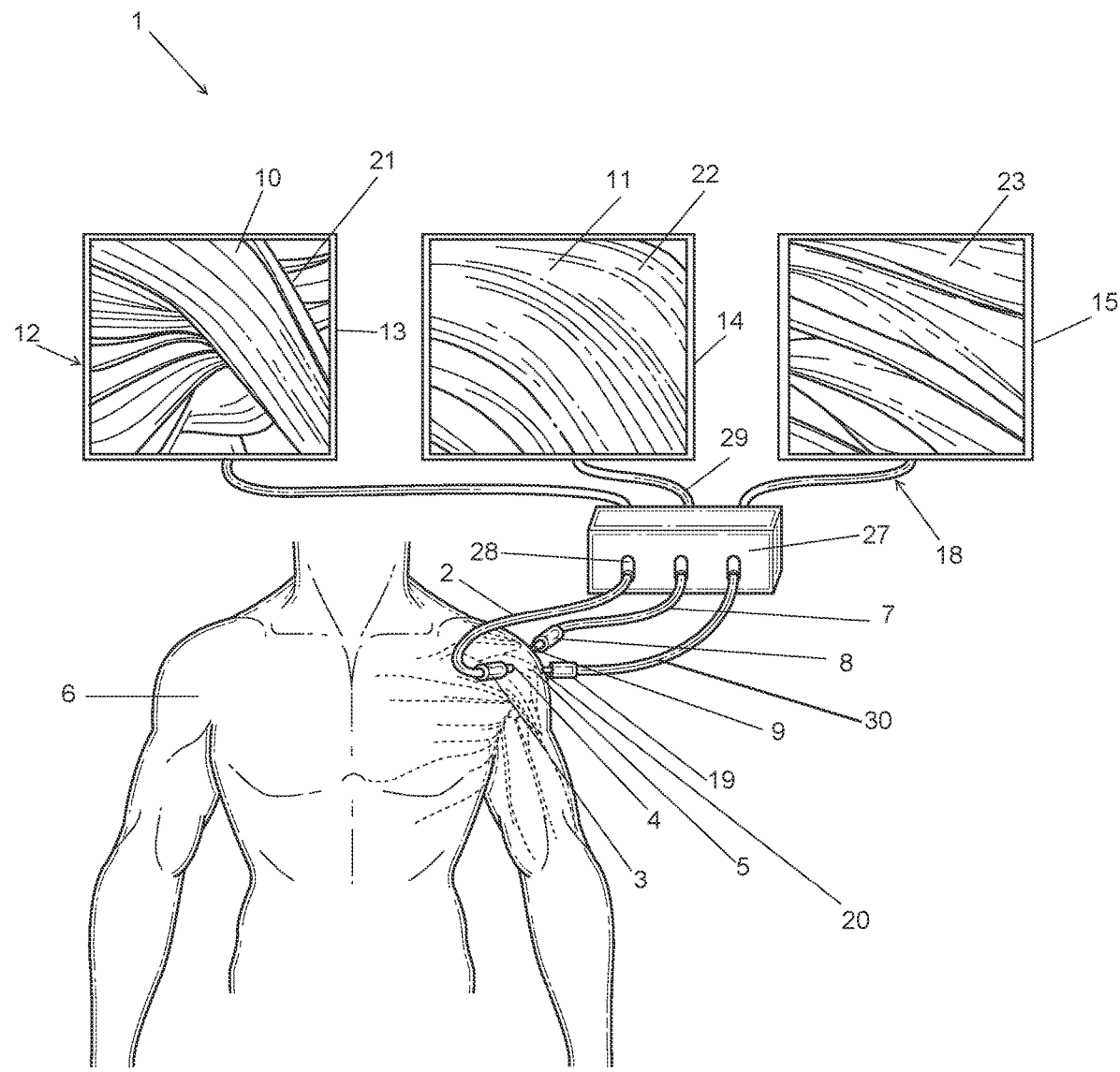
FIG. 1 shows a non-limiting example of a visualization system in accordance with some embodiments of the present invention.

It should be understood that the present invention includes a variety of aspects, which may be combined in different ways. The following descriptions are provided to list elements and describe some of the embodiments of the present invention. These elements are listed with initial embodiments; however, it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments is not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide an operating visualization system comprising: a first endoscope with a first camera placed at a first position near a surgical target area of a patient; a second endoscope with a second camera placed at a second position near said surgical target area of said patient; a first image from said first camera at said first position of said surgical target area of said patient; a second image from said second camera at said second position of said surgical target area of said patient; and perhaps even a first and second live-view image display of said first image and said second image of said surgical target area of said patient. Other embodiments may include a method of digitally visualizing an endoscopic operation comprising the steps of: providing a surgical target area of a patient; inserting a first endoscope with a first camera placed at a first position near said surgical target area of said patient; inserting a second endoscope with a second camera placed at a second position near said surgical target area of said patient; live viewing a first image from said first camera at said first position of said surgical target area of said patient; live viewing a second image from said second camera at said second position surgical target area of said patient; and perhaps even performing an operation on said patient while viewing said first and second images.

Embodiments of the present invention may provide an enhanced visualization system and methods of digitally visualizing an endoscopic operation for various procedures such as with arthroscopic and even laparoscopic procedures. A system may provide multiple camera views of a joint or other space so that a surgeon may view the joint on a screen or multiple screens. Multiple angled camera views perspectives perhaps at viewed once or even alternating, may provide enhanced visualization of the area being operated on such as a joint, laparoscopic space, or the like.

An operating visualization system (1) may be a system that can assist in viewing an area for surgery via an endoscopic procedure or the like. In some embodiments, a first endoscope (2) with a first camera (3) may be placed or even inserted at a first position (4) near a surgical target area (5) of a patient (6) perhaps as understood in FIG. 1. A second endoscope (7) with a second camera (8) may be placed or even inserted at a second position near (9) a surgical target area (5) of a patient (6). In embodiments, a third endoscope

(30) with a third camera (19) may be placed or even inserted at a third position (20) near a surgical target area of a patient. An endoscope may be an instrument that may be used as a viewing system for examining an inner part of the body which may be a slender, tubular optical instrument or the like. Another instrument may be used for biopsy or surgery or the like and may be attached to or separate from an endoscope. An endoscope may include a camera or other device which can capture an image or images. A surgical target area of a patient may be an area of an inside of a body where surgery or other procedures may need take place. This could be for an endoscopic procedure, a laparoscopic procedure, a biopsy, or the like and may be an endoscopic area, a laparoscopic area, joint, other areas of the body, or the like. A patient may be an animal, a mammal, a human, or the like.

To assist in helping a surgeon adequately view a surgical target area, each endoscope may be placed at different positions near a surgical target area. This may include a first position, a second position, and a third position where the endoscope and camera view thereof can show different angles of the surgical target area. Of course, in some embodiments, there may be more than three endoscopes and three cameras used and any number may be used. Endoscopes placed near an area may include a point that is a short distance from the area, a point that includes an angle of an area, and the like.

A first image (10) from a first camera at a first position of a surgical target may be generated as well as a second image (11) from a second camera at a second position of a surgical target area. A third image may be generated from a third camera at a third position of a surgical target area. Such images may be displayed perhaps in a display such as a first and second live-view image display (12). Such display of images may be in real-time or almost real time such as to assist the surgeon in live viewing the various images to perform an operation on the patient which viewing the images. In some embodiments, a display may be separate displays (13), (14), (15) perhaps of the images of the surgical target area of the patient.

Inserting endoscopes into a patient may be through portals (not shown) such as a first endoscope may be placed in a first portal, a second endoscope may be placed in a second portal, etc. Portals may allow an endoscope to be put inside a body through an incision made in the skin perhaps when keyhole surgery may be done. Endoscopes may be put into a body through a mouth or down a throat or the like. A portal may be a device which may be inserted into a body through an incision which may include a cannula or the like.

A system may include a camera box (27) perhaps with multiple inputs (28) and outputs (29) which may be wired (18), corded, wireless, cordless, or the like which can provide a wired connection or a wireless connection or the like between a camera and a display. A first, second, and even a third display or more may be viewed simultaneously so that each display can be viewed at the same time; may be viewed alternating in that each view is alternating with the others, may be synthesized in that a single image of the views from each of these angles may be constructed. As such, embodiments of the present invention may provide simultaneously live viewing first image and second images or more; alternating a view of a first image and second images or more; viewing a synthesized image of first image and second images or more; and the like. Images and views from a first position, a second position, and perhaps even a third position may show a posterior view (21), a lateral view (22), and even an anterior view (23) of a surgical target area of a patient. Other views can be obtained as desired.

Figure 4:
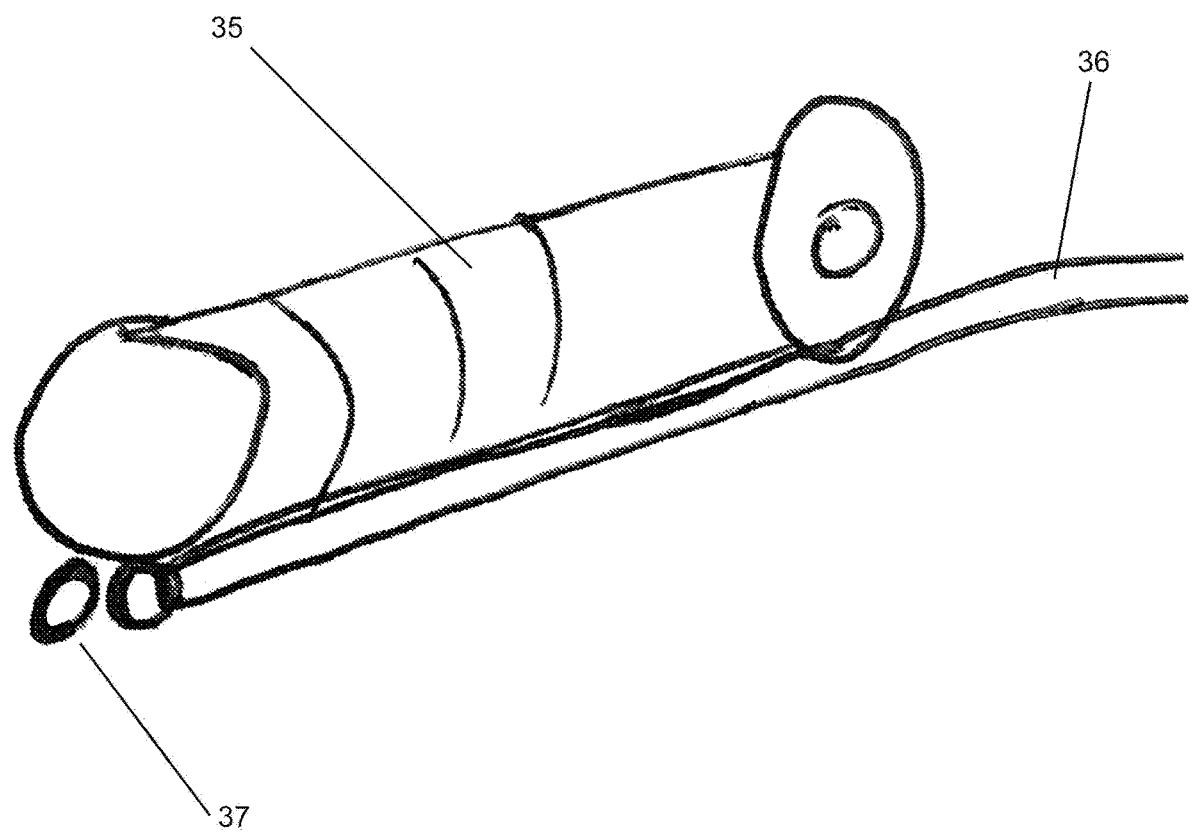
FIG. 4 shows a non-limiting example of a cannula coupled with a small tube and an LED camera in accordance with some embodiments of the present invention.

Embodiments of the present invention may include a cannula (35) coupled to a small tube (36). One end of the small tube (36) may contain an LED camera (37), such as shown in FIG. 4. The scope may be integrated into the cannula (35) or a deeper instrument, including for example, an elevator. Color control synergy and/or surface mapping may also be utilized.

Figure 5:
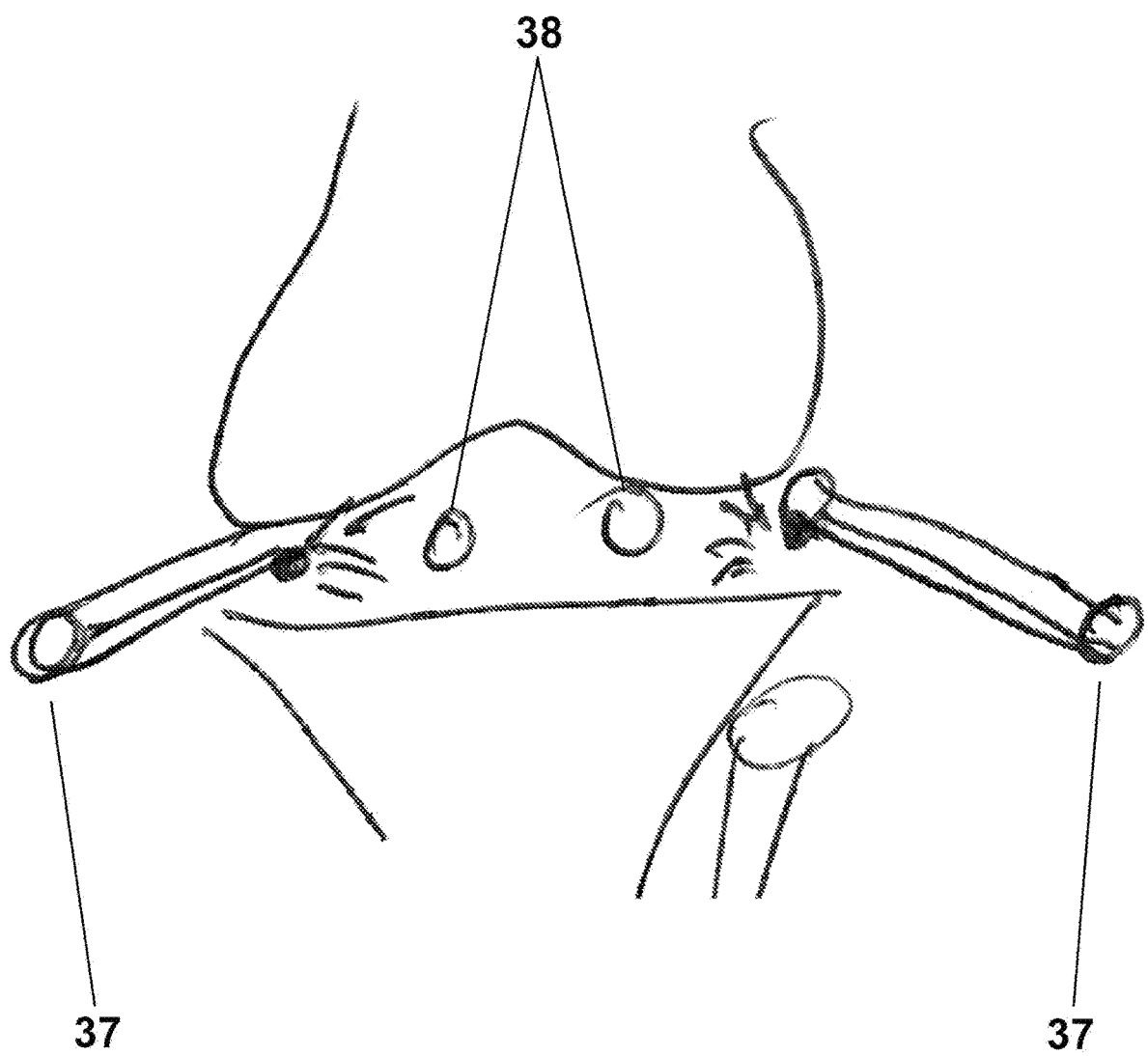
FIG. 5 shows a non-limiting example of two LED cameras in use adjacent to two work portals during a surgical procedure in accordance with some embodiments of the present invention.

Additional embodiments of the present invention, such as shown in FIG. 5, may include two LED cameras (37) positioned adjacent to work portals (38) during a surgical procedure. These LED cameras (37) may be manually controlled or may be hands-free. The use of two cameras simultaneously may allow the use of video "stitch" technology to display a three-dimensional view, which may allow for a "hands-free" orthoscopy.

Figure 6:
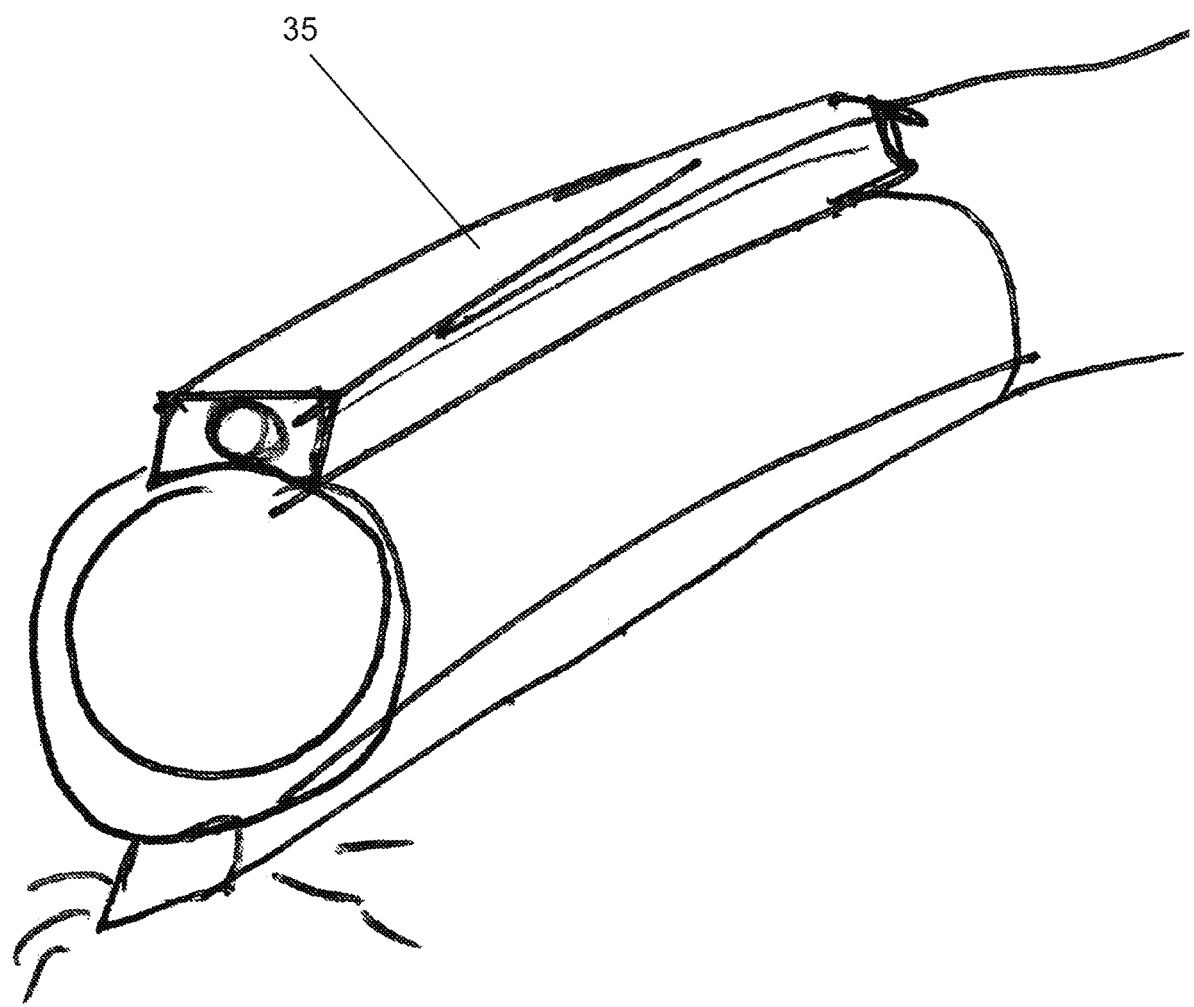
FIG. 6 shows a non-limiting example of a cannula integrated camera in accordance with some embodiments of the present invention.

As shown in FIG. 6, embodiments of the present invention may include a cannula integrated camera. A scope may include a camera coupled at one location and an LED light coupled at a second, perhaps opposite location. A user may remove a scope and insert a cannula. These systems may utilize a 120V power plug.

Embodiments of the present invention may include multiple smaller diameter scopes and even intraoperative visualization screens perhaps to allow for the simultaneous viewing of the pathology and even the repair process from multiple angles without a need to switch the single scope between portals.

Figure 2:
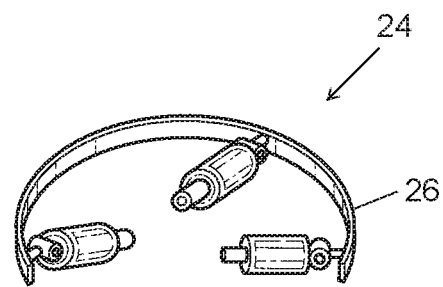
FIG. 2 shows a non-limiting example of endoscopes interlocked with each other in accordance with some embodiments of the present invention.
Figure 3:
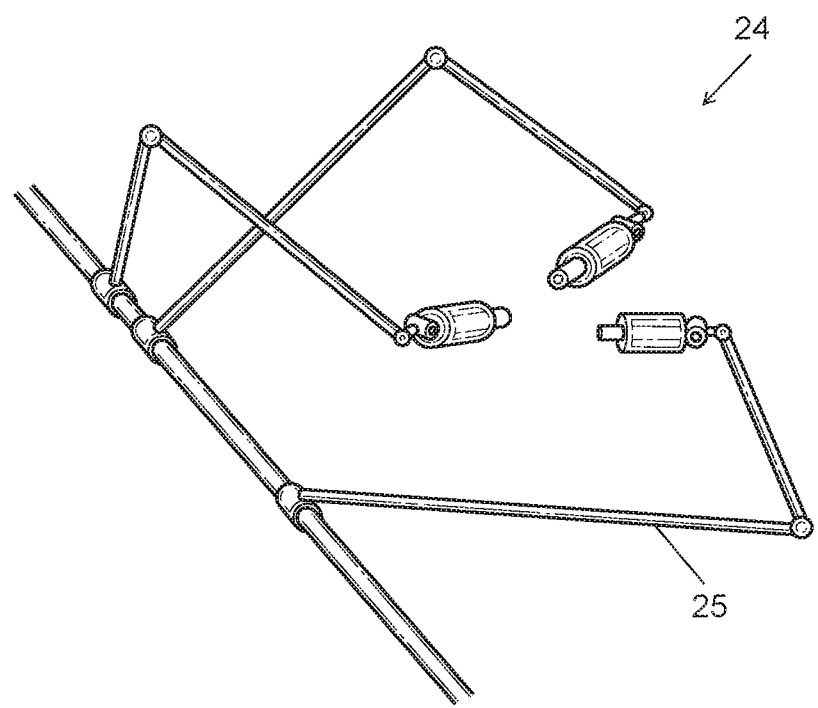
FIG. 3 shows a non-limiting example of cameras stabilized with adjustable arms in accordance with some embodiments of the present invention.

Embodiments of the present invention may include a stabilizing component (24) to hold the endoscopes and cameras perhaps in a fixed position and which may allow clean images. A stabilization component may be an adjustable stabilization device, multiple adjustable stabilization devices, an adjustable secure arm (25), more than one adjustable secure arm, or the like which may allow scopes to be positioned perhaps in a stable but adjustable manner as may be understood from FIG. 3. A stabilizing component may be a connected securement support (26) which can stabilize a first camera, a second camera, and even a third camera or more which may be understood from FIG. 2.

Additional embodiments of the present invention may include an omni scope which may vary from approximately 105 degrees to approximately 140 degrees. It may have an approximately 30/70 degree button push.

Additional embodiments of the present invention may include an office scope which may also include:
a vision scope
Trice medical
scope
Biol. injection Embodiments of the present invention may include the following features:
Disposable
14 gauge
capability to plug into a tablet or other electronic device
capability to work with a curved cannula or a straight cannula Embodiments of the present invention may include a scope on a cannula, or a cannula-scope, which may also include
sensors of any measurement including micro-sized
use of office development
real-time video stitching
stabilization, including the use of gyros on the end of the
camera to help stabilize and unite Alternate embodiments of the present invention may also include:
- a peel pack
- a perc slap kit
- a prototype vial, possibly cannulated or curved
- a separate injection port
- a PRP delivery system
- targeted injections As can be easily understood from the foregoing, the basic concepts of the present invention may be embodied in a variety of ways. It involves both visualization techniques as well as devices to accomplish the appropriate visualization of joints. In this application, the visualization techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. As one example, terms of degree, terms of approximation, and/or relative terms may be used. These may include terms such as the words: substantially, about, only, and the like. These words and types of words are to be understood in a dictionary sense as terms that encompass an ample or considerable amount, quantity, size, etc. as well as terms that encompass largely but not wholly that which is specified. Further, for this application if or when used, terms of degree, terms of approximation, and/or relative terms should be understood as also encompassing more precise and even quantitative values that include various levels of precision and the possibility of claims that address a number of quantitative options and alternatives. For example, to the extent ultimately used, the existence or non-existence of a substance or condition in a particular input, output, or at a particular stage can be specified as substantially only x or substantially free of x, as a value of about x, or such other similar language. Using percentage values as one example, these types of terms should be understood as encompassing the options of percentage values that include 99.5%, 99%, 97%, 95%, 92% or even 90% of the specified value or relative condition; correspondingly for values at the other end of the spectrum (e.g., substantially free of x, these should be understood as encompassing the options of percentage values that include not more than 0.5%, 1%, 3%, 5%, 8% or even 10% of the specified value or relative condition, all whether by volume or by weight as either may be specified. In context, these should be understood by a person of ordinary skill as being disclosed and included whether in an absolute value sense or in valuing one set of or substance as compared to the value of a second set of or substance. Again, these are implicitly included in this disclosure and should (and, it is believed, would) be understood to a person of ordinary skill in this field. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "scope" should be understood to encompass disclosure of the act of "scoping"—whether explicitly discussed or not—and, conversely, were there effectively disclosure of the act of "scoping", such a disclosure should be understood to encompass disclosure of a "scope" and even a "means for scoping." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the information disclosure statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the grip devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such processes, methods, systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method of digitally visualizing an arthroscopic operation comprising the steps of:
    providing an arthroscopic joint surgical target area of a patient;
    providing a first portal and a second portal near said arthroscopic joint surgical target area of said patient;
    inserting a first endoscope with a first camera through said first portal, wherein said first camera is connected to a camera box;
    placing said first endoscope with said first camera at a first fixed position near said arthroscopic joint surgical target area of said patient;
    maintaining said first endoscope with said first camera at said first fixed position during a procedure on said patient;
    inserting a second endoscope with a second camera through said second portal, wherein said second camera is connected to said camera box;
    placing said second endoscope with said second camera at a second fixed position near said arthroscopic joint surgical target area of said patient;
    maintaining said second endoscope with said second camera at said second fixed position during said procedure on said patient;
    capturing in real-time a first image from said first camera at said first fixed position at said first portal of said arthroscopic joint surgical target area of said patient;
    capturing in real-time a second image from said second camera at said second fixed position at said second portal of said arthroscopic joint surgical target area of said patient;
    inserting a third endoscope with a third camera through a third portal near said surgical target area of said patient, wherein said third camera is connected to said camera box;
    placing said third endoscope with said third camera at a third fixed position near said arthroscopic joint surgical target area of said patient, wherein said third fixed position is different than said first and second fixed positions;
    capturing in real-time a third image from said third camera at said third fixed position of said arthroscopic joint surgical target area of said patient;
    simultaneously displaying said first, second, and third images of said arthroscopic joint surgical target area utilizing said camera box connected to said first, second, and third cameras; and
    wherein said first image, said second image, and said third image comprise images showing a posterior view, a lateral view, and an anterior view of said arthroscopic joint surgical target area of said patient.

2. The method as described in claim 1 wherein said second portal is at a different location from said first portal in said patient.

3. The method as described in claim 1 wherein said step of simultaneously displaying said first and second images of said arthroscopic joint surgical target area utilizing said camera box connected to said first and second cameras comprises a step of simultaneously displaying a synthesized image of said first image and said second image of said arthroscopic joint surgical target area utilizing said camera box connected to said first and second cameras.

4. The method as described in claim 1 and further comprising inserting an instrument into said arthroscopic joint surgical target area through said first portal or said second portal.

5. The method as described in claim 1 and further comprising steps of:
    inserting an instrument with said first endoscope and said first camera through said first portal; and
    inserting another instrument with said second endoscope and said second camera through said second portal.

6. The method as described in claim 1 and further comprising a step of providing at least one additional portal near said arthroscopic joint surgical target area of said patient.

* * * * *